United States Patent [19]
Hodosh et al.

[11] Patent Number: 5,807,334
[45] Date of Patent: Sep. 15, 1998

[54] FLUID DISPENSING APPARATUS

[76] Inventors: Milton Hodosh, 2 Harian Dr., Providence, R.I. 02906; Fitz-Eugene Dixon Newbold, 56 Winchester Dr., North Scituate, R.I. 02857

[21] Appl. No.: 546,382

[22] Filed: Oct. 20, 1995

[51] Int. Cl.$^6$ ................................................ A61M 37/00
[52] U.S. Cl. ........................ 604/131; 604/155; 604/224
[58] Field of Search ................................ 604/131, 151, 604/152, 154, 155, 224; 128/DIG. 12; 74/421 A, 360, 89.17

[56] References Cited

U.S. PATENT DOCUMENTS

| | | | |
|---|---|---|---|
| 2,574,263 | 11/1951 | Hinds | 604/155 |
| 3,395,704 | 8/1968 | Frey et al. | 604/154 X |
| 3,768,472 | 10/1973 | Hodosh et al. | |
| 3,811,442 | 5/1974 | Maroth . | |
| 4,273,122 | 6/1981 | Whitney et al. | 604/155 X |
| 4,560,979 | 12/1985 | Rosskopf . | |
| 4,627,835 | 12/1986 | Fenton, Jr. | 604/154 X |
| 4,668,220 | 5/1987 | Hawrylenko . | |
| 4,676,122 | 6/1987 | Szabo et al. | 604/154 X |
| 4,787,893 | 11/1988 | Villette . | |
| 4,897,080 | 1/1990 | Hamidi . | |
| 5,034,003 | 7/1991 | Denance . | |
| 5,176,646 | 1/1993 | Kuroda . | |
| 5,232,449 | 8/1993 | Stern et al. | 604/154 |
| 5,322,511 | 6/1994 | Armbruster et al. | 604/155 |

*Primary Examiner*—Max Hindenburg
*Assistant Examiner*—Pamela L. Wingood
*Attorney, Agent, or Firm*—Salter & Michaelson

[57] ABSTRACT

A fluid dispenser includes a hollow housing having an elongate chamber formed therein. A power supply is located within the chamber of the housing, the power supply being in electrical communication with a motor also located within the chamber of the housing. A switch, accessible from outside the housing, is in electrical communication with the power supply and motor for selectively operating the motor from a non-operable condition to an operable condition. A gear train is driven by a drive shaft of the motor, the gear train being located within the chamber of the housing and having a plurality of gears. At least one of the gears defines a slow speed gear which is rotatable at a relatively slow rate of speed and at least another of the gears defines a fast speed gear which is rotatable at a relatively fast rate of speed. A rack member is selectively engagable with one of the slow and fast speed gears for moving the rack member linearly from a position in which the end portion is spaced from a carpule containing fluid to be dispensed to a position in which the end portion engages a carpule piston so as to effect the dispensing of fluid from the carpule at a controlled rate. Further provided is means for selectively engaging one of the slow and fast speed gears with the teeth of the rack member.

12 Claims, 7 Drawing Sheets

FLUID DISPENSING APPARATUS

BACKGROUND AND SUMMARY OF THE INVENTION

This invention relates generally to fluid dispensers, and more particularly to a fluid dispensing apparatus capable of dispensing anesthesia (e.g., novocaine) at a slow and controlled rate.

During certain surgical and dental procedures, and particularly the latter, it is common practice to administer an anesthetic, such as lidocaine, in order to temporarily anesthetize sensitive nerves so that the patient will not be compelled to endure pain. However, the administration of the anesthetic is, to most patients, extremely unpleasant and often painful. It is relatively well-known that the primary cause of pain and discomfort attendant to the administration of a liquid anesthetic, such as lidocaine, is the fact that the conventional injection apparatus administers the anesthetic too quickly and without sufficient uniformity. It is further relatively well-known that if the anesthetic is administered slowly and uniformly, almost on a drop-by-drop basis, remarkably little or no pain or discomfort results.

Regardless of the specific nature of the injection, the fact of the matter is that there are numerous types of injections in which it is highly desirable to make the injection on an extremely slow and uniform basis. Where such requirements exist, hand syringes depend upon the manual dexterity of the person administering the same and have proven unsatisfactory.

Reference can be made to applicant's U.S. Pat. No. 3,768,472 dated Oct. 30, 1973, this patent disclosing a hand-held, gun-shaped fluid dispenser which is operated by a pressurized gas, such as carbon dioxide, that is introduced in the dispenser from either an outside source or through an internally received cartridge. This apparatus, while being somewhat more effective than prior apparatuses and methods, has several shortcomings. For example, because the injection of the fluid is achieved by pressurized gas, the uniformity of flow is sometimes inconsistent due to pressure surges and drops. Additionally, the initial expense of providing a source of pressurized gas is somewhat cost prohibitive. Similarly, pressurized cartridges are also expensive. Moreover, it is not advisable to have high pressure gases proximate to one's face.

Thus, there is presently a need for a fluid dispensing apparatus which can deliver anesthetic in a consistent, uniform, and nearly painless manner while being cost-efficient to manufacture and operate.

Accordingly, among the several objects of the present invention are the provision of an improved fluid dispensing apparatus which is capable of automatically dispensing fluid from a carpule in a slow, controlled and uniform manner; the provision of such an apparatus which is capable of aspirating; the provision of such an apparatus which is battery operated thereby freeing the apparatus from external cords and the like; the provision of such an apparatus which incorporates a rechargeable battery; the provision of such an apparatus having a pen light feature for illuminating the space inside the patient's mouth; the provision of such an apparatus which is light and compact; the provision of such an apparatus which is simple in design and cost-efficient to manufacture; and the provision of such an apparatus which is durable in use.

In general, a fluid dispenser of the present invention for dispensing fluid from a carpule having an axially slidable piston comprises a hollow housing having an elongate chamber formed therein. The housing extends generally along an axis, and is constructed and arranged to be gripped comfortably within a person's hand. A carpule receiving member, which is attached to the housing at one end thereof, has means for receiving a needle at its other opposite end. The receiving member is adapted to receive a carpule having fluid therein which is ejected through the needle. It is detachable for sterilization or replacement by a sterile disposable component. A power supply is located within the chamber of the housing, the power supply being in electrical communication with a motor also located within the chamber of the housing. A switch, accessible from outside the housing, is in electrical communication with the power supply and motor for selectively operating the motor from a non-operable condition in which the power supply is electrically disconnected from the motor to an operable condition in which the power supply is electrically connected to the motor and supplies power thereto. A gear train is driven by a drive shaft of the motor, the gear train being located within the chamber of the housing and having a plurality of gears. At least one of the gears defines a slow speed gear which is rotatable at a relatively slow rate of speed and at least another of the gears defines a fast speed gear which is rotatable at a relatively fast rate of speed. A rack member, disposed within the chamber of the housing along the axis, comprises an elongate body having an end portion engagable with the piston of the carpule and teeth formed on a side thereof which are selectively engagable with one of the slow and fast speed gears for moving the rack member linearly from a position in which the end portion is spaced from the carpule piston to a position in which the end portion engages the carpule piston so as to effect the dispensing of fluid from the carpule and through the needle at a controlled rate. Further provided is means for selectively engaging one of the slow and fast speed gears with the teeth of the rack member.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention.

Corresponding reference numerals designate corresponding parts throughout the several views of the drawings.

DETAILED DESCRIPTION OF THE PREFERRED EMBODIMENT

Figure 1:
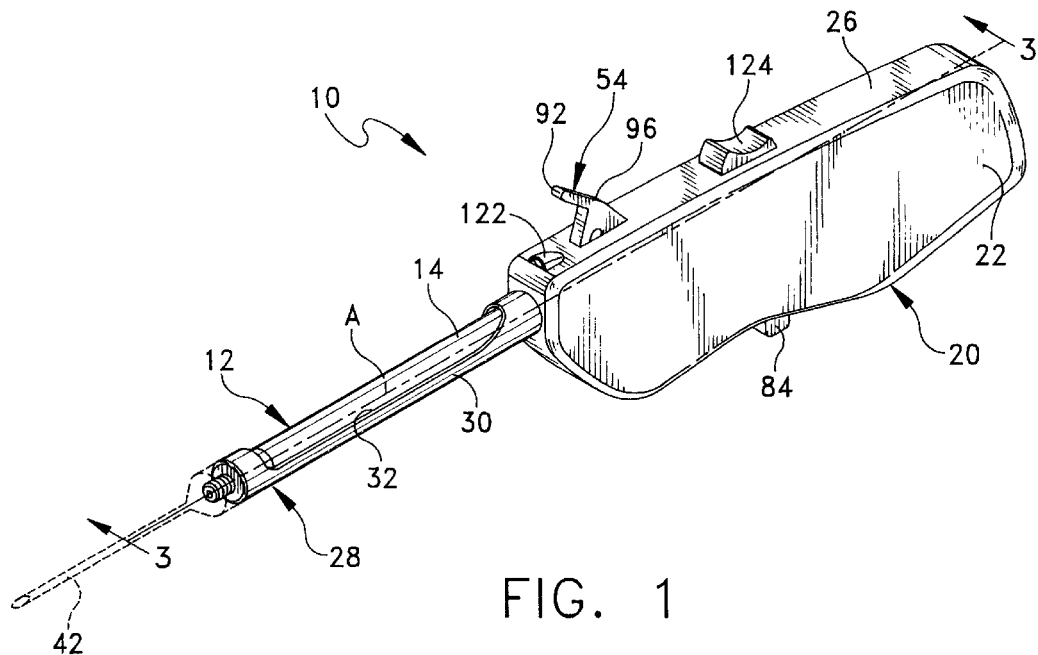
FIG. 1 is a perspective view of a fluid dispensing apparatus of the present invention.
Figure 2:
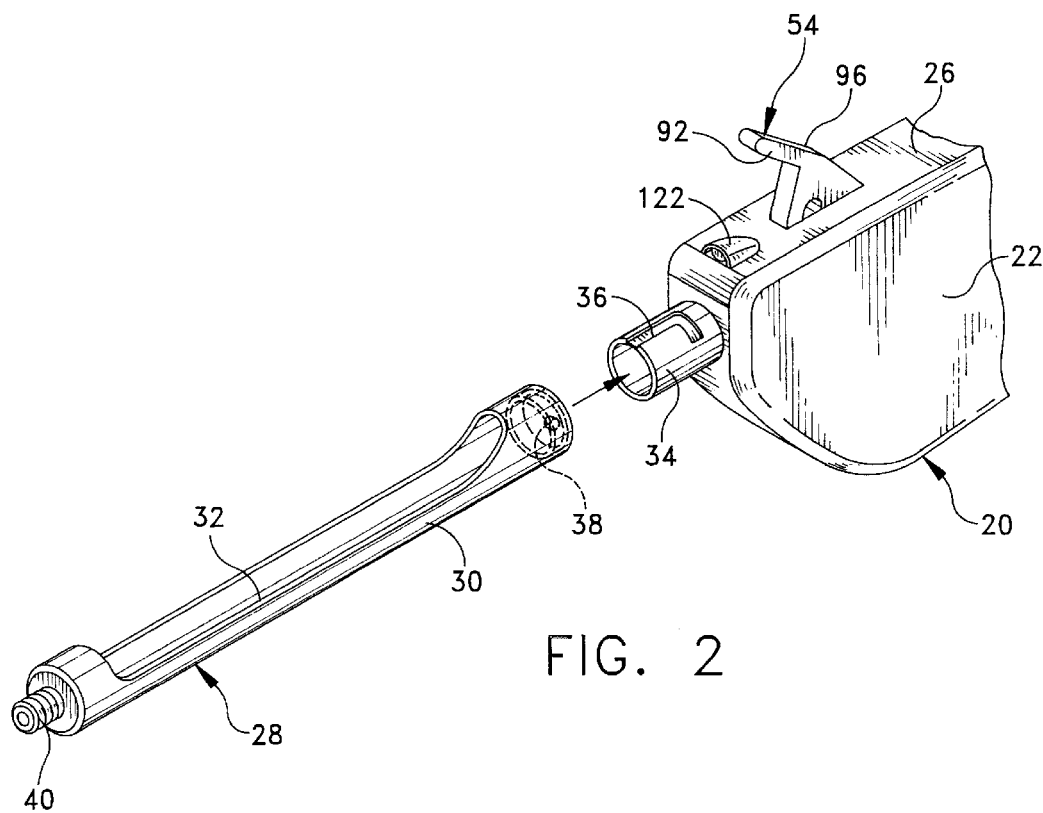
FIG. 2 is an enlarged perspective view of a portion of the apparatus illustrating the mounting of a carpule receiving member onto a housing of the apparatus.
Figure 3:
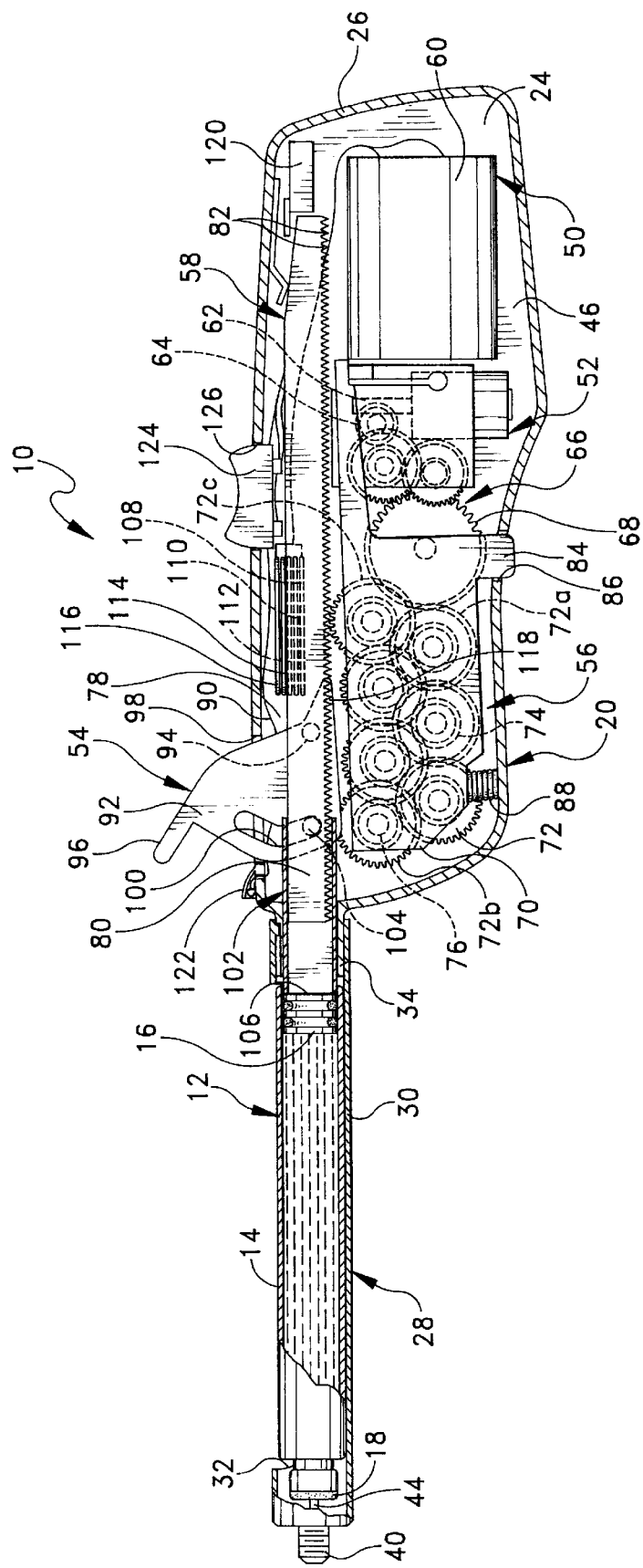
FIG. 3 is a cross-sectional view taken along line 3—3 of FIG. 1.

Referring now to the drawings, and more particularly to FIGS. 1 through 3, there is generally indicated at 10 a fluid dispensing apparatus of the present invention which is designed to dispense fluid from a carpule, generally indicated at 12. The carpule 12 is of the type having a cylindrical body 14 which is made from any suitable translucent material, such as clear plastic or glass, and an axially slidable piston 16 provided at an open end of the body 14. At the other end of the body 14, a rubber gasket 18 closes the open end. In the present invention, the carpule 12 preferably contains a suitable anesthetic for use during dental work. The manner in which the fluid is dispensed from the carpule 12 will be described in greater detail as the description of the apparatus 10 proceeds.

As shown, the apparatus 10 comprises an elongate housing generally indicated at 20 which extends along an axis A and has two relatively planar side walls 22, 24 and an outer peripheral wall 26 which interconnects the two side walls 22, 24. The arrangement is such that any one of the side walls 22, 24 is integrally formed with the outer peripheral wall 26 and the other of the side walls is attached to the other side wall 26 by means of screw fasteners (not shown). This construction is well-known in the art although the actual shape of the housing is not disclosed in any of the aforementioned prior art. Preferably, the housing 20 is fabricated from rigid material, such as plastic. As illustrated throughout the drawings, the housing 20 of the fluid dispensing apparatus 10 differs significantly from other prior art devices, such as the gun-shaped dispenser disclosed in U.S. Pat. No. 3,768,472, in that it is relatively compact and can be held in the operator's hand much like a pen. This results in the operator being able to hold the apparatus 10 with greater ease and dexterity.

The forward end of the housing 20 is constructed to receive a carpule receiving member, generally indicated at 28, which can be fabricated from autoclavable plastic or from reusable stainless steel. Preferably, the receiving member 28 is removably mounted on the housing 20 so that it can be removed for cleaning and sterilization, or to be replaced by a sterilized disposable member 28. As most clearly illustrated in FIG. 2, the carpule receiving member 28 comprises an outer cylindrical wall 30 that has an elongate slot 32 formed therein which is sized for receiving the carpule 12. This also enables the person administering the anesthetic to view the carpule 12 which is received within the slot 32 of the receiving member 28. The carpule receiving member 28 is releasably mounted on the housing 20 by a bayonet type of mount or the like.

More specifically, the housing 20 of the apparatus 10 includes a sleeve 34 which is mounted axially along axis A, the sleeve 34 including an L-shaped slot 36 formed therein. The wall 30 of the receiving member 28 is sized to receive the sleeve 34 therein when mounting the receiving member 28 to the housing 20. A detent member 38 is formed on the inner surface of the wall 30, the detent member 38 being received in the L-shaped slot 36 when mounting the receiving member 28 thereto. The receiving member 28 is secured to the housing 20 by axially sliding it over the sleeve 34 with the detent member 38 in the long leg of the L-shaped slot 36 until the sleeve 34 is nearly completely disposed within the cylindrical wall 30. At this point, the receiving member 28 is rotated clockwise for firmly securing the receiving member 28 to the housing 20, the detent member 38 being held secure by the sleeve 34 within the short leg of the L-shaped slot 36.

Figure 4:
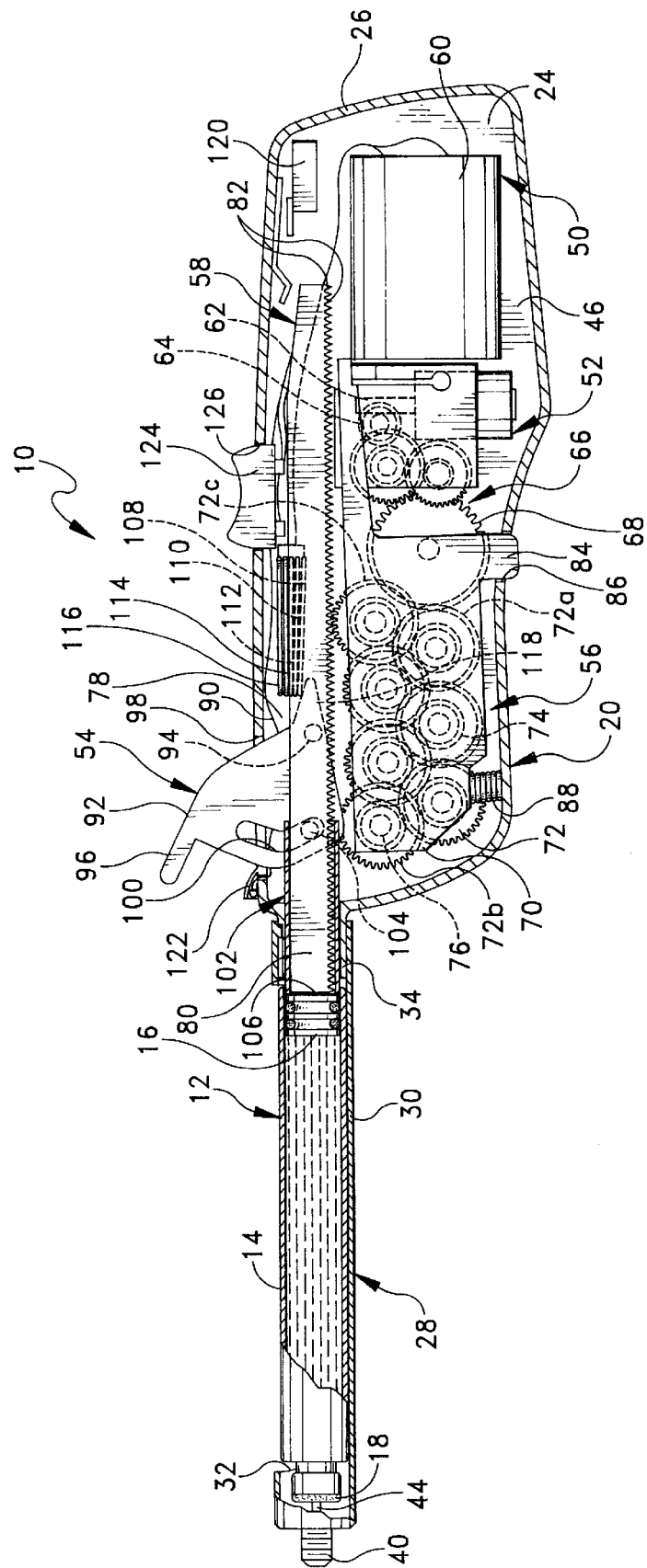
FIG. 4 is a cross-sectional view similar to FIG. 3 illustrating the apparatus in an aspirating mode.
Figure 5:
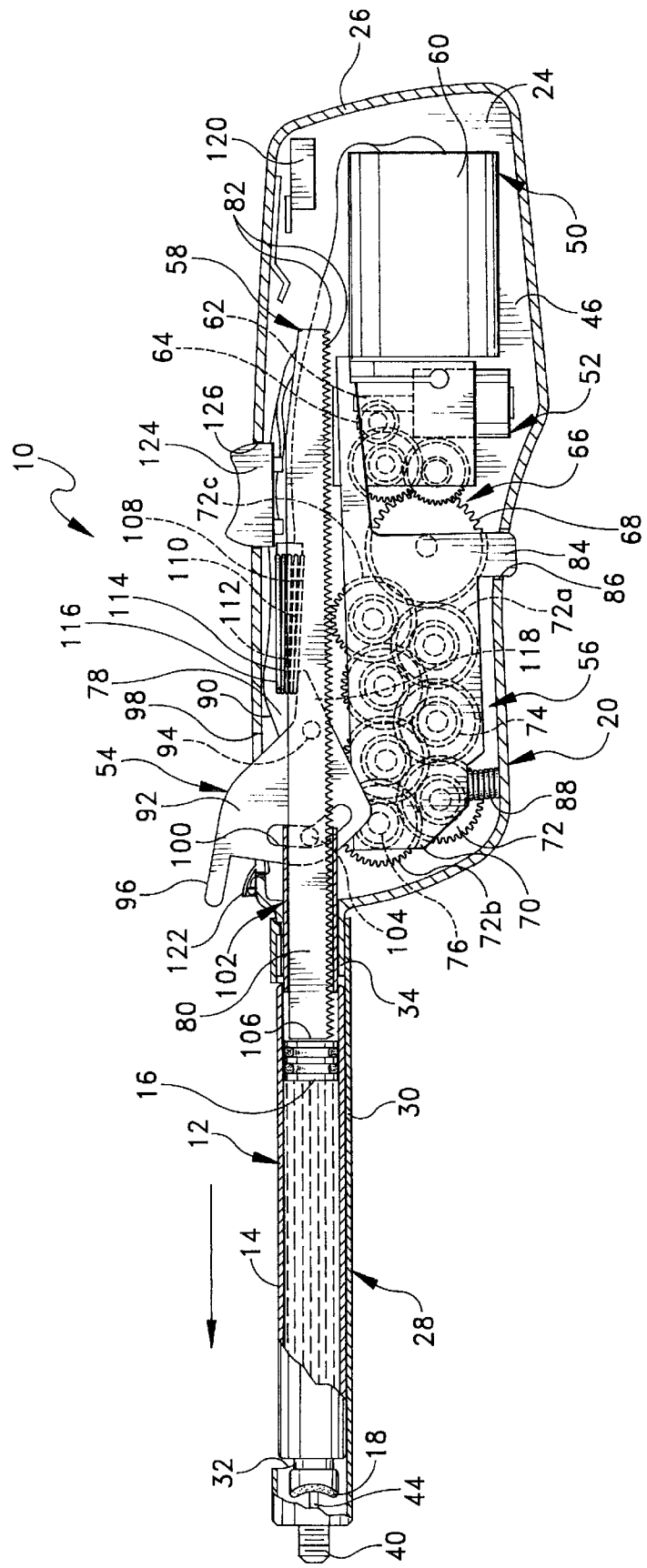
FIG. 5 is a cross-sectional view similar to FIGS. 3 and 4 illustrating the apparatus in fast forward operating mode.
Figure 6:
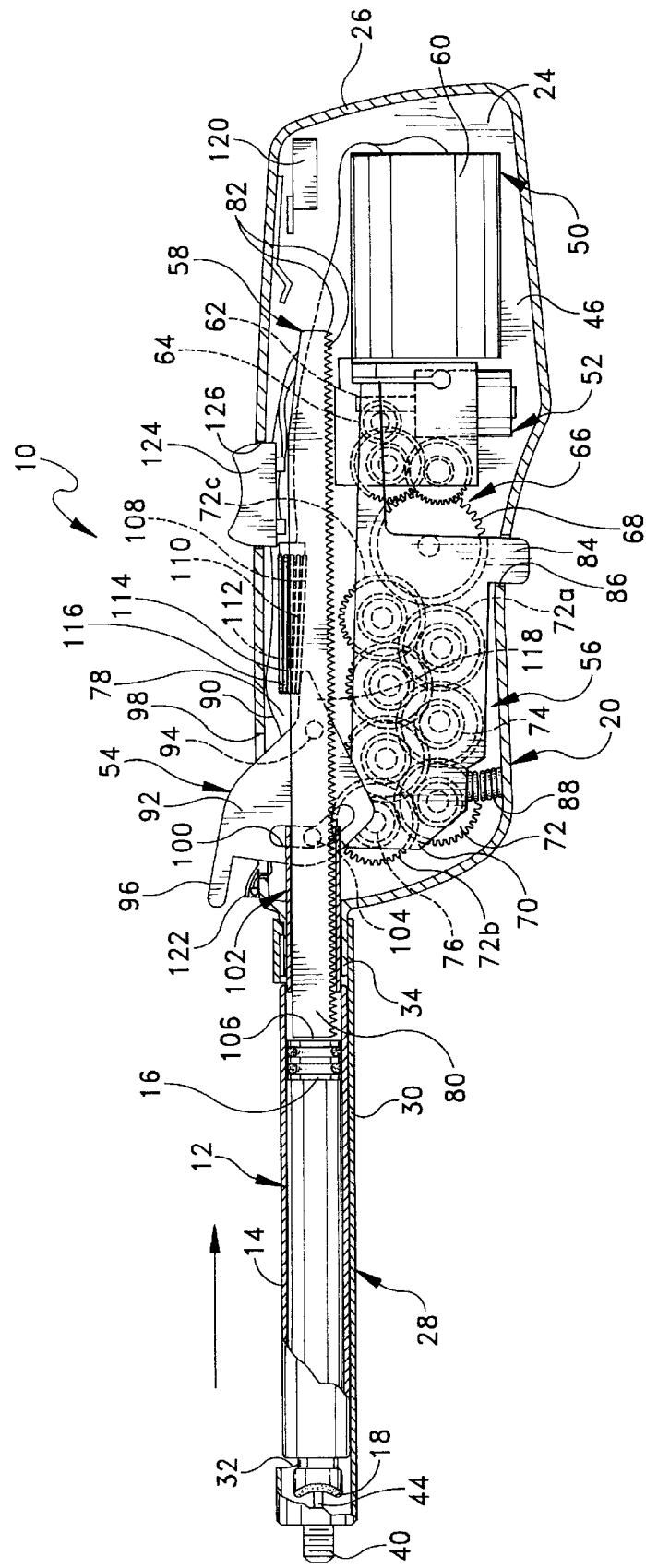
FIG. 6 is a cross-sectional view similar to FIGS. 3 through 5 illustrating the apparatus in slow forward operating mode.

The forward end of the carpule receiving member 28 has a cylindrical threaded portion 40 with outer male threads formed therein for releasably securing a needle 42 thereto (see FIG. 1). As shown, the needle has an elongate cylindrical member and in internal needle portion (not shown) which punctures the rubber gasket 18 of the carpule in the well-known manner. The purpose of this construction is for enabling the operator of the apparatus 10 to remove the needle 42 and replace it after each use. Integrally formed with the threaded portion 40 is an annular stem portion 44 which deflects the rubber gasket 18 of the carpule 12 when the carpule 12 is disposed within the receiving member 28. The stem portion 44 is designed to receive therein the internal needle portion of the needle. FIGS. 4 through 6 illustrate the stem portion 44 deflecting the rubber gasket 18 of the carpule 12.

Turning now to FIGS. 3 through 7, the housing 20 of the apparatus 10 is of hollow construction having an elongate chamber 46 formed therein which contains the component parts for applying an axial force on the piston 16 of the carpule 12 for dispensing fluid at a slow and uniform rate therefrom. More specifically, the apparatus 10 includes, within the chamber 46 of the housing 20, a power supply, generally indicated at 50, a motor, generally indicated at 52, which is energized by the power supply 50, a switch, generally indicated at 54, for turning on and off the motor 52, a gear train, generally indicated at 56, for moving a rack member, generally indicated at 58, axially along axis A to compress the piston 16 of the carpule 12. Preferably, the power supply 50 includes a rechargeable battery 60; however, the apparatus 10 can include a power cord (not shown) for electrically connecting the apparatus 10 to an electrical wall outlet. The provision of a rechargeable battery 60 enables the operator of the apparatus 10 to freely move and operate it without the constrictions of an attached cord.

Preferably, the motor 52 is a single speed motor operable by means described below to achieve one of three speeds. The motor 52 has a core body and a drive shaft 62 which is rotatably driven by the motor 52 at one of three speeds. The drive shaft 62 has a worm gear 64 mounted thereon which engages and drives a group of six gears, generally designated 66, rotatably mounted on three shafts within the chamber 46. The arrangement is such that one large diameter gear and one small diameter gear are mounted on a shaft. The shafts of the spur gears are suitably mounted within the chamber 46 of the housing 20. The largest of the group of gears 66, gear 68, drives the gear train 56. The positioning and arrangement of the group of spur gears 66 need not be described in great detail since a person skilled in the art could use any number of gears and position them at any number of locations within the chamber 46 of the housing 20 for driving the gear train 56.

The gear train 56 includes a frame 70 which supports seven larger gears, each indicated at 72, and seven smaller gears, each indicated at 74, respectively mounted on seven rotatably mounted shafts, each indicated at 76. As shown, the large spur gear 68 of the group of gears 66 engages the bottom, right-hand larger gear 72a of the gear train 56 for driving the rotation of all of the gears 72, 74 of the gear train 56. The arrangement is such that the gear train 56 includes at least one large gear (the top, left-hand gear) designated 72b which defines a slow speed gear that is rotatable at a relatively slow rate of speed, and at least one other large gear (the top, right-hand gear) designated 72c which defines a fast speed gear that is rotatable at a relatively fast rate of speed. These two gears 72b, 72c are engagable with the rack member 58 as illustrated in FIG. 3 and FIG. 6, respectively.

Figure 7:
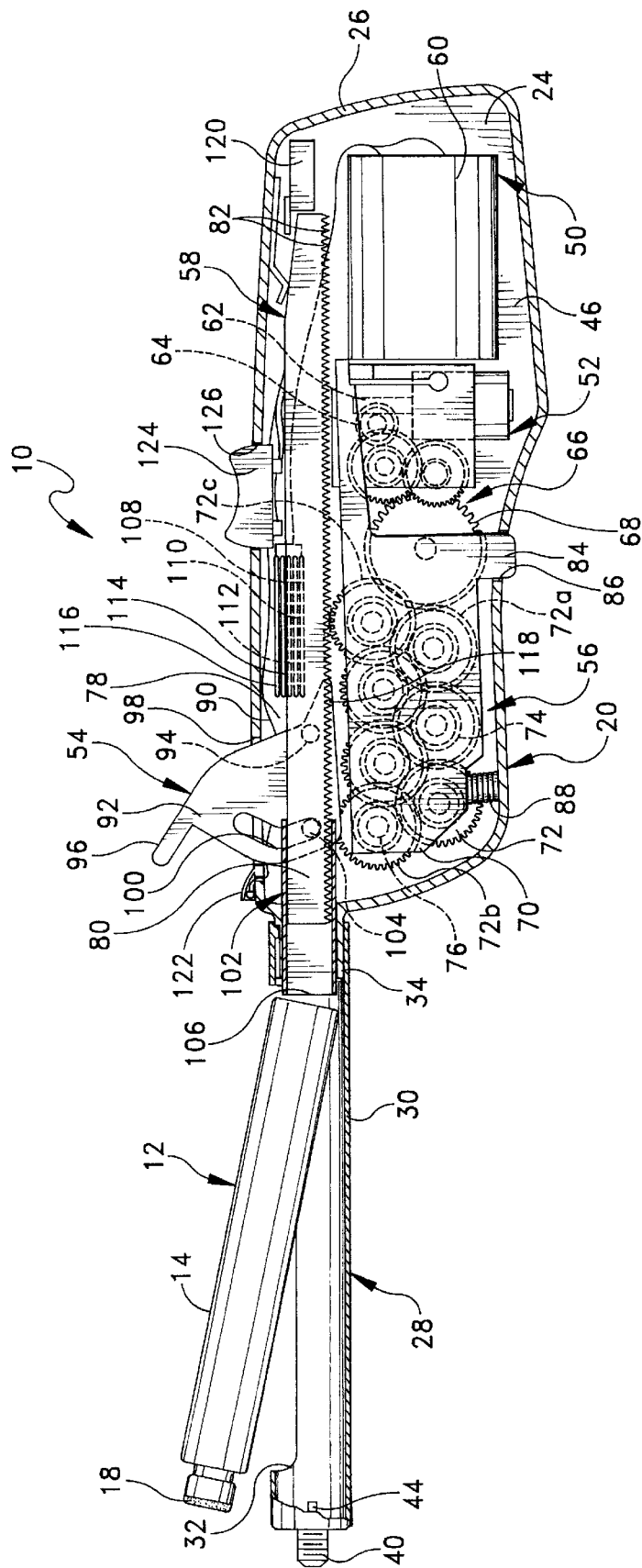
FIG. 7 is a cross-sectional view similar to FIG. 3 through 6 illustrating the apparatus in fast reverse operating mode.

More specifically, the rack member 58, which is axially slidable with a channel (not shown) formed on the interior surfaces of the housing 20, comprises an elongate body 78 having an end portion 80 which is engagable with the piston 16 of the carpule 12 and teeth 82 formed on a side of the body 78 which are selectively engagable with one of the slow and fast speed gears. FIGS. 3 and 7 illustrate the rack member 58 in a retracted position in which it is completely positioned within the chamber 46 of the housing 20 and the end portion 80 of the rack member 58 is spaced from the carpule piston 16. FIGS. 4 through 6 illustrate the rack member 58 in an extended position in which one of the slow and fast speed gears 72b, 72c engages the teeth 82 of the rack member 58 for moving it linearly along axis A to a position in which the end portion 80 engages the carpule piston 16. The rack member 58 moves linearly along axis A towards the carpule 12 for causing the dispensing of fluid from the carpule 12 and through the needle 42 at a slow and controlled rate.

The frame 70 is pivotally mounted within the chamber 46 of the housing 20 so as to effect the selective engagement of either the slow speed gear 72b or the fast speed gear 72c with the teeth 82 of the rack member 58. The frame 70 has an outwardly protruding member 84 which is accessible from outside of the housing 20 through an opening 86 formed in the outer peripheral wall 26 of the housing 20 for moving the frame 70 between a first position in which the slow speed gear 72b is engaging the teeth 82 of the rack member 58 and a second position in which the fast speed gear 72c is engaging the teeth 82. As shown, a spring 88, engagable at one of its ends with the frame 70 and at its other opposite end with the wall 26 of the housing 20, is further provided for biasing the frame 70 to its first position in which the slow speed gear 72b drives the rack member 58. By engaging the member 84 of the frame 70 and pivoting the frame 70 upwardly, the bias of spring 88 is overcome and the fast speed gear 72c engages or meshes with the teeth of the rack member 58. The fast speed gear 72c preferably rotates at approximately 16 RPM (thereby resulting in the rack member moving at 25 inches per minute). By virtue of the five intermediate pairs of gears 72, 74 disposed between the slow speed and fast speed gears 72b, 72c, the speed of the slow speed gear 72b is reduced to approximately 2 RPM (thereby resulting in the rack member moving at 3 inches per minute).

The switch 54 is suitably electrically connected with the battery 60 and the motor 52 by wires 90 in the well-known fashion for selectively operating the motor 52 from a non-operable condition in which the battery 60 is electrically disconnected from the motor 52 to an operable condition in which the battery 60 is electrically connected to the motor 52 and supplies power thereto. The switch 54 includes a depressible lever 92 pivotally mounted on the housing 20 by a protrusion 94 which is held captive by the housing 20 in such a manner that an engaging portion 96 of the lever 92 is accessible from outside the housing 20. The engaging portion 96 extends through an opening 98 formed in the outer peripheral wall 26 of the housing 20 and is capable of being pressed by the operator of the apparatus 10 by the operator's forefinger. Thus, the amount of force required to pivot the lever 92 downwardly into the chamber 46 of the housing 20 is relatively slight thereby enabling the apparatus 10 to be held like a pen and not like a gun.

The lever 92 further has a curved or arcuate portion having a slot 100 formed therein. The curved portion of the lever 92 is engagable with an axially slidable, annular sleeve generally indicated at 102 which is disposed around the rack member 58 between the curved portion of the lever 92 and the body 14 of the carpule 12. The arrangement is such that when the engaging portion 96 of the lever 92 is pressed downwardly as illustrated in FIG. 4, the curved portion engages the annular sleeve 102 for axially moving it slightly towards the carpule 12 thereby dispensing a small amount of fluid from the carpule.

More specifically, the annular sleeve 102 has a detent member 104 which is received in the slot 100 of the lever 92 and rides within the slot as the lever is pressed downwardly. As the lever 92 moves downwardly, the detent member 104 of the sleeve 102 moves axially towards the carpule 12 whereby the end 106 of the sleeve 102 engages the body 14 of the carpule 12. Conversely, as the lever 92 is spring biased upwardly, the detent member 104 is withdrawn back into the housing 20 thereby moving the sleeve 102 axially away from the carpule 12. Thus, as illustrated in FIG. 4, when the curved portion of the lever 92 engages the detent member 104 of the sleeve 102 in response to a person applying a downward force on the engaging portion 96 of the lever 92, the end 106 of the sleeve 102 slides axially along axis A so as to cause the slight movement of the body 14 (e.g., approximately 1.5 mm) thereby compressing the resilient gasket 18 and dispensing a small amount of fluid from the carpule 12 through the needle 42. If the needle 42 is slightly penetrating the tissue of the patient requiring anesthetizing, by releasing the lever 92, a small amount of fluid is drawn back through the needle 42 and into the carpule 12. By releasing the lever 92, the camming action of the detent member 104 within the slot 100 causes the rearward movement of the sleeve 102. This aspirating step enables the operator of the apparatus 10 giving the injection to determine whether the needle 42 is penetrating a major blood vessel.

As mentioned briefly above, the apparatus' motor 52 can operate at one of three speeds, thus enabling the apparatus 10 to operate at six separate speeds, i.e., three "slow" speeds and three "fast" speeds, depending upon whether the slow or fast speed gear 72b, 72c is engaging the rack member 58. To change the speed of the motor 52, the lever 92 is either slightly pivoted, moderately pivoted or nearly fully pivoted (see FIG. 5 which illustrates the nearly fully pivoted position), for respectively selecting a slow, intermediate and fast motor speed. The switch 54 further comprises three sets of thin, elongate contacts which are in electrical communication with the battery 60 and the motor 52, and are operable for activating the motor 52 in one of its three respective speeds. As shown, there are five contacts, contacts 108, 110 constituting a first set of contacts, contacts 110, 112 constituting a second set of contacts, and contacts 112, 114 constituting a third set of contacts. The fifth contact 116 is a spare which is provided with the sets of contacts. The lever has a tail portion 118 which is engagable with the contacts 108, 110, 112, 114 and 116 when the engaging portion 96 is pressed downwardly by the person operating the apparatus 10. Thus, by moving the lever 92 to its slightly pivoted position, the first set of contacts 108, 110 are engaged by the tail portion 118 for operating the motor 52 at a first, relatively slow speed. Similarly, by moving the lever 92 to its moderately and nearly fully pivoted positions with the tail portion 118 (see FIGS. 5 and 6 for the nearly fully pivoted position), the second set of contact 110, 112 and third set of contacts 112, 114 are engaged for operating the motor 52 at a second (intermediate) speed and a third (fast) speed, respectively.

A limit switch 120, mounted within the chamber 46 of the housing 20 at its rearward end, is provided for cutting off the motor 52 upon being engaged by the other end of the rack member 58. This occurs when the rack member 58 is in its fully retracted position.

A further feature of the present invention is the provision of a pen light 122 mounted on the forward end of the housing 20 for illuminating the space in front of the dispensing apparatus 10 (i.e., the patient's mouth). The pen light 122 can be turned on and off by any suitable means, such as by a switch (not shown), and draws its energy from the battery 60. The electrical hook-up of the pen light 122 with the battery 60 can be accomplished in any conventional, well-known fashion.

In order to return the rack member 58 to its retracted position, a reversing switch 124, which is in electrical communication with the motor 52, is further provided. The reversing switch 124 extends through an opening 126 formed in the outer peripheral wall 26 of the housing 20 right behind the lever 42. The reversing switch 124 simply reverses the rotation of the shaft 62 of the motor, thereby reversing the rotation of the gears 72, 74 of the gear train 56. The reversing switch 124 enables the operator of the apparatus 10 to control the speed of the retraction of the rack member 58 in any one of six speeds; however, it has been found that best results are obtained by engaging the fast speed gear 72c with the teeth 82 of the rack member 58 and by pressing the lever 92 so that the third set of contacts 112, 114 are in engagement thereby retracting the rack member 58 into the housing 20 as quickly as possible.

Figure 8:
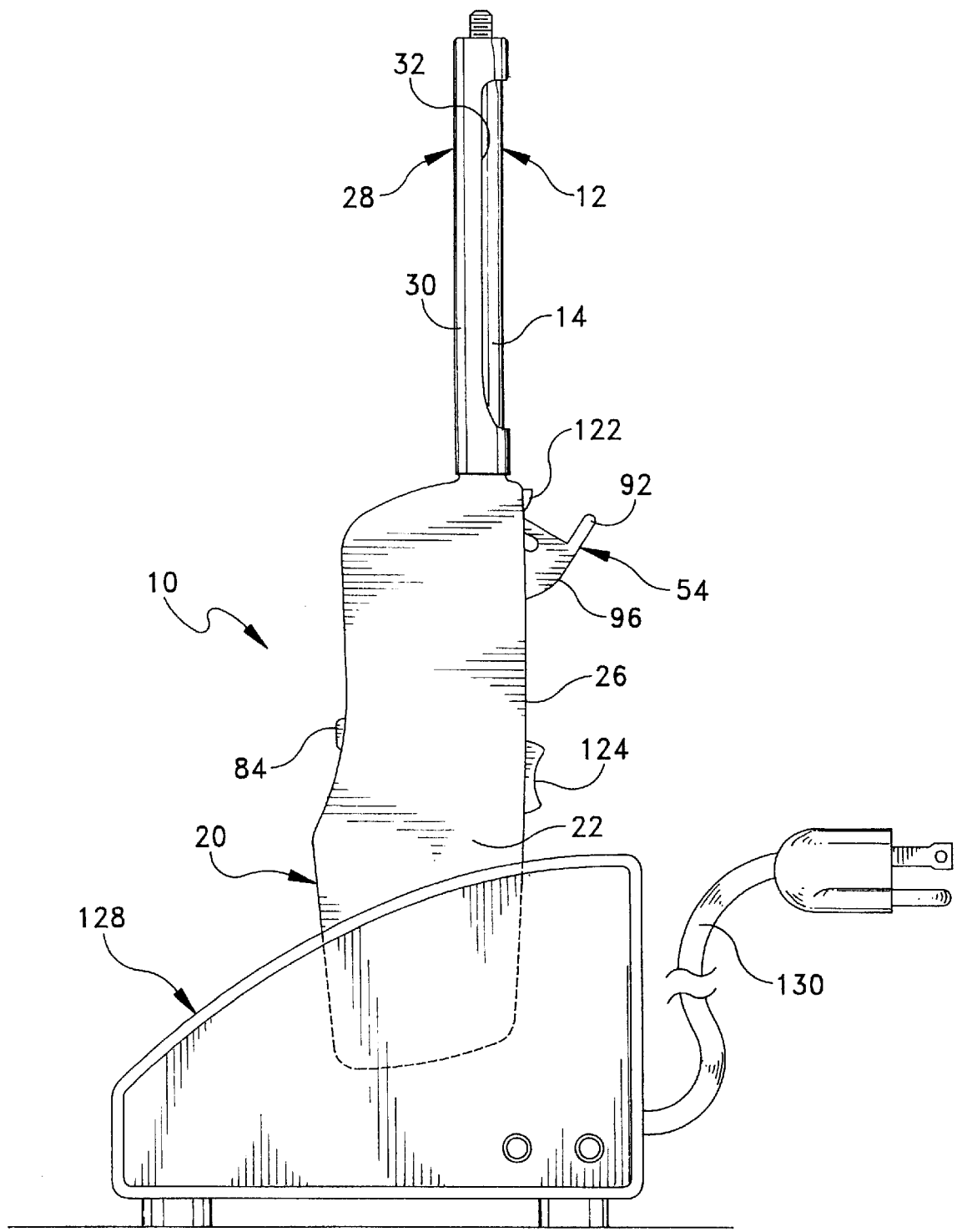
FIG. 8 is an elevational view of the apparatus seated in a battery recharging device.

Referring now to FIG. 8, there is illustrated the apparatus 10 of the present invention seated within a battery charging device, generally indicated at 128, for recharging the battery 60. The device 128 is preferably fabricated from any rigid material (e.g., plastic) and includes a plug 130 which plugs into a standard electrical wall outlet. Although not illustrated, the housing 20 of the apparatus 10 may be provided with a plug or receptacle which is in electrical communication with the battery 60 for supplying energy to the battery 60 when it is seated in the device 128. Such a system is well-known in the art of battery operated tools which require having their batteries recharged. A manifold design can be used to recharge multiple batteries at once and the apparatus can have lights indicated the need for battery recharging as is well-known in other apparatuses.

During use, the apparatus 10, having a charged battery 60, is assembled for use by mounting the carpule receiving member 28 onto the forward end of the housing 20. At this time, a needle 42 can be screwed onto the threaded portion 40 of the receiving member 28. Both of these component parts are removable from the housing 20 and from each other for sterilization purposes, or to be exchanged between patient use for a sterilized replacement member 28. Next, a carpule 12 is inserted through the slot 32 of the receiving member 28 in a position where it rests inside the receiving member 28 (see FIGS. 3 through 6). When inserting the carpule 12 into the receiving member 28, it is important to note that the rack member 58 is in its retracted position.

The rack member 58 is then moved linearly towards the piston 16 of the carpule 12 in either the slow or fast speed mode, depending upon the distance between the end portion 80 of the rack member 58 and the piston 16 of the carpule 12. Once the end portion 80 is in engagement with the piston 16 of the carpule 12, the lever 92 is slightly pivoted so as to engage the curved portion of the lever 92 with the detent member 104 of the sleeve 102, thereby moving the sleeve 102 linearly towards the carpule 12 for dispensing a small amount of fluid. Aspiration can be achieved by releasing the lever 92 thereby drawing fluid back into the carpule 12. The provision of this mechanical aspiration feature of the present invention makes it especially easy to perform the aspiration function.

To inject the fluid into the tissue penetrated by the needle 42, the lever 92 is pressed downwardly so as to engage the first set of contacts 108, 110 thereby energizing the motor 52. Preferably, the frame 70 of the gear train 56 is in its normally biased position wherein the slow speed gear 106 engages the teeth 82 of the rack member 58. The person operating the apparatus 10 can quicken the amount of fluid being dispensed into the tissue area by further pressing the lever 92 downwardly thereby engaging the second set of contacts 110, 112 or the third sets of contacts 112, 114. Since the slow speed gear 72b is driving the rack member 58, the speed of the movement of the rack member 58 is not extremely fast. It should be noted that by providing a completely mechanical actuating system, wherein pneumatic or hydraulic actuators are not involved, slow and uniform delivery of fluid is ensured.

Once the injection is given, and the needle 42 is removed from the tissue area of the patient's mouth, the rack member 58 is withdrawn into the chamber 46 of the housing 20 by pressing the reversing switch 124, moving the frame 70 of the gear train 56 to its fast mode by applying a force on the outwardly protruding member 84 of the frame 70, and pressing the lever downwardly so as to engage the third set of contacts 112, 114. By following these steps, the rack member 58 is quickly withdrawn into the chamber 46 of the housing 20. Upon engaging the limit switch 120, power to the motor 52 is cutoff and the rack member 58 is in its fully retracted position.

At this point, the carpule 12 is removed from the receiving member 28 in the manner illustrated in FIG. 7 and the carpule receiving member can be removed from the housing 20 for sterilization. When finished, the apparatus 10 is placed back in the battery recharging device 128 for recharging the battery 60.

The apparatus 10 of the present invention is an automated fluid delivery apparatus which can employ several motor technologies, including direct current motors, stepper motors and piezoelectric motors. The advantage of the construction of the present invention is that the apparatus delivers fluid in a controlled, uniform, and smooth manner which is free of surge that is present with manual injection devices. Hand or manual syringes emit fluids less slowly, less smoothly, and sporadically. The apparatus 10 releases fluids at a slower, more uniform rate and the fluid, instead of balling up (tending to gather in a mass) as is the case with hand syringes. The application of fluid in a controlled manner enables the fluid to be gradually absorbed by the tissues and nerves. This makes the apparatus 10 of the present invention more effective since there is less pressure exerted on the tissues and nerves, and the fluid does not dissect or force its way into them. Thus, the apparatus 10 substantially eliminates the pain caused by the surging of fluid associated with manual injections.

Furthermore, there is an improved safety factor due to the slow, uniform flow of fluid. Not only does the application of fluid with apparatus 10 minimize pain, but it also acts to prevent shocking the patient's vascular and nervous systems. The apparatus 10 allows for aspiration so the clinician applying the fluid can determine whether the needle is penetrating a blood vessel. And even if the needle has entered the blood vessel, the fluid is administered so slowly by the apparatus 10 that vagal/vagal type of reactions are avoided.

Needle puncture pain is lessened owing to the technique of allowing the anesthetic to flow slowly and continuously ahead of the penetrating needle. This application diminishes pain that could occur from the fast needle penetrating associated with manual needles. Also, reloading with second, third, etc., carpules of anesthetic (or medication) is readily accomplished due to the quick withdrawal feature of the apparatus which enables the rack member 58 to be withdrawn within the housing 20.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A fluid dispensing apparatus for dispensing fluid from a carpule having an axially slidable piston, said apparatus comprising:

a hollow housing having an elongate chamber formed therein, said housing extending generally along an axis and being constructed and arranged to be gripped within a person's hand;

a carpule receiving member which is attached to said housing at one end thereof, said carpule receiving member having means for receiving a needle at its other opposite end and being adapted to receive a carpule having fluid therein which is ejected through the needle;

a power supply located within the chamber of the housing;

a motor energized by said power supply, said motor being located within the chamber of the housing and having a drive shaft which is rotatable driven;

a switch accessible from outside the housing and being in electrical communication with said power supply and motor for selectively operating said motor from a non-operable condition in which the power supply is electrically disconnected from the motor to an operable condition in which the power supply is electrically connected to the motor and supplies power thereto;

a gear train driven by said drive shaft of the motor, the gear train being located within the chamber of the housing and having a plurality of gears, at least one of said gears defining a slow speed gear which is rotatable at a relatively slow rate of speed and at least another of said gears defining a fast speed gear which is rotatable at a relatively fast rate of speed;

a rack member disposed within the chamber of the housing along said axis, said rack member comprising an elongate body having an end portion engagable with said piston of the carpule and teeth formed on a side thereof which are selectively engagable with one of said slow and fast speed gears for moving the rack member linearly from a position in which the end portion is spaced from the carpule piston to a position in which the end portion engages the carpule piston so as to effect the dispensing of fluid from the carpule and through the needle at a controlled rate; and means for selectively engaging one of the slow and fast speed gears with the teeth of the rack member, said engaging means comprising a frame which houses the plurality of gears of said gear train, said frame being pivotally attached to the housing and having an outwardly protruding member which is accessible from outside the housing for moving the frame between a first position in which the slow speed gear is engaging the teeth of the rack member and a second position in which the fast speed gear is engaging the teeth.

2. A fluid dispensing apparatus as set forth in claim 1, said engaging means further comprising means for biasing said frame to its first position.

3. A fluid dispensing apparatus as set forth in claim 2, said biasing means comprising a spring engagable at one of its ends with the frame and at its other opposite end with the housing.

4. A fluid dispensing apparatus for dispensing fluid from a carpule having an axially slidable piston, said apparatus comprising:

a hollow housing having an elongate chamber formed therein, said housing extending generally along an axis and being constructed and arranged to be gripped within a person's hand;

a carpule receiving member which is attached to said housing at one end thereof, said carpule receiving member having means for receiving a needle at its other opposite end and being adapted to receive a carpule having fluid therein which is ejected through the needle, said carpule receiving member being releasably attached to the housing for removal to sterilize the receiving member;

a power supply located within the chamber of the housing;

a motor energized by said power supply, said motor being located within the chamber of the housing and having a drive shaft which is rotatable driven;

a switch accessible from outside the housing and being in electrical communication with said power supply and motor for selectively operating said motor from a non-operable condition in which the power supply is electrically disconnected from the motor to an operable condition in which the power supply is electrically connected to the motor and supplies power thereto;

a gear train driven by said drive shaft of the motor, the gear train being located within the chamber of the housing and having a plurality of gears, at least one of said gears defining a slow speed gear which is rotatable at a relatively slow rate of speed and at least another of said gears defining a fast speed gear which is rotatable at a relatively fast rate of speed;

a rack member disposed within the chamber of the housing along said axis, said rack member comprising an elongate body having an end portion engagable with said piston of the carpule and teeth formed on a side thereof which are selectively engagable with one of said slow and fast speed gears for moving the rack member linearly from a position in which the end portion is spaced from the carpule piston to a position in which the end portion engages the carpule piston so as to effect the dispensing of fluid from the carpule and through the needle at a controlled rate; and means for selectively engaging one of the slow and fast speed gears with the teeth of the rack member.

5. A fluid dispensing apparatus as set forth in claim 4, said carpule receiving member having a bayonet-type mount comprising a detent member formed on its end which is receivable within a slot formed in an annular sleeve which is attached to the housing.

6. A fluid dispensing apparatus for dispensing fluid from a carpule having an axially slidable piston, said apparatus comprising:

a hollow housing having an elongate chamber formed therein, said housing extending generally along an axis and being constructed and arranged to be gripped within a person's hand;

a carpule receiving member which is attached to said housing at one end thereof, said carpule receiving member having means for receiving a needle at its other opposite end and being adapted to receive a carpule having fluid therein which is ejected through the needle;

a power supply located within the chamber of the housing;

a motor energized by said power supply, said motor being located within the chamber of the housing and having a drive shaft which is rotatable driven;

a switch accessible from outside the housing and being in electrical communication with said power supply and motor for selectively operating said motor from a non-operable condition in which the power supply is electrically disconnected from the motor to an operable condition in which the power supply is electrically connected to the motor and supplies power thereto, said switch comprising a depressible lever pivotally mounted on said housing;

a gear train driven by said drive shaft of the motor, the gear train being located within the chamber of the housing and having a plurality of gears, at least one of said gears defining a slow speed gear which is rotatable at a relatively slow rate of speed and at least another of said gears defining a fast speed gear which is rotatable at a relatively fast rate of speed;

a rack member disposed within the chamber of the housing along said axis, said rack member comprising an elongate body having an end portion engagable with said piston of the carpule and teeth formed on a side thereof which are selectively engaaable with one of said slow and fast speed gears for moving the rack member linearly from a position in which the end portion is spaced from the carpule piston to a position in which the end portion engages the carpule piston so as to effect the dispensing of fluid from the carpule and through the needle at a controlled rate; and means for selectively engaging one of the slow and fast speed tears with the teeth of the rack member.

7. A fluid dispensing apparatus as set forth in claim 6, said lever having a curved portion engagable with an axially slidable, annular sleeve which is disposed between the curved portion of the lever and the piston of the carpule, the arrangement is such that when the lever is pressed, the curved portion of the lever engages the annular sleeve for axially moving said annular sleeve towards the piston of the carpule thereby dispensing a small amount of fluid.

8. A fluid dispensing apparatus as set forth in claim 7, said annular sleeve having a detent member engagable with the curved portion of the lever through a slot formed therein and an end portion engagable with the piston of the carpule.

9. A fluid dispensing apparatus as set forth in claim 6, said switch further comprising three sets of contacts operably activating three speeds of the motor, said lever having a tail portion engagable with the three sets of contacts for selectively operating the motor in one of its three speeds.

10. A fluid dispensing apparatus as set forth in claim 1, said housing having a pen light mounted on its forward end for illuminating the space in front of the dispensing apparatus.

11. A fluid dispensing apparatuses for dispensing fluid from a carpule having an axially slidable piston, said apparatus comprising:

a hollow housing having an elongate chamber formed therein, said housing extending generally along an axis and being constructed and arranged to be gripped within a person's hand;

a carpule receiving member which is attached to said housing at one end thereof, said carpule receiving member having means for receiving a needle at its other opposite end and being adapted to receive a carpule having fluid therein which is ejected through the needle;

a power supply located within the chamber of the housing;

a motor energized by said power supply, said motor being located within the chamber of the housing and having a drive shaft which is rotatable driven;

a switch accessible from outside the housing and being in electrical communication with said power supply and motor for selectively operating said motor from a non-operable condition in which the power supply is electrically disconnected from the motor to an operable condition in which the power supply is electrically connected to the motor and supplies power thereto;

a gear train driven by said drive shaft of the motor, the gear train being located within the chamber of the housing and having a plurality of gears, at least one of said gears defining a slow speed gear which is rotatable at a relatively slow rate of speed and at least another of said gears defining a fast speed gear which is rotatable at a relatively fast rate of speed, said drive shaft of the motor having a worm gear mounted thereon, said worm gear engaging and driving a spur gear rotatably mounted on a shaft within the chamber and engagable with a gear of said gear train;

a rack member disposed within the chamber of the housing along said axis, said rack member comprising an elongate body having an end portion engagable with said piston of the carpule and teeth formed on a side thereof which are selectively engagable with one of said slow and fast speed gears for moving the rack member linearly from a position in which the end portion is spaced from the carpule piston to a position in which the end portion engage the carpule piston so as to effect the dispensing of fluid from the carpule and through the needle at a controlled rate; and means for selectively engaging one of the slow and fast speed gears with the teeth of the rack member.

12. A fluid dispensing apparatus for dispensing fluid from a carpule having an axially slidable piston, said apparatus comprising:

a hollow housing having an elongate chamber formed therein, said housing extending generally along an axis and being constructed and arranged to be gripped within a person's hand;

a carpule receiving member which is attached to said housing at one end thereof, said carpule receiving member having means for receiving a needle at its other opposite end and being adapted to receive a carpule having fluid therein which is ejected through the needle;

power supply means located within the chamber of the housing;

motor means energized by said power supply means, said motor means being located within the chamber of the housing;

a switch accessible from outside the housing and being in electrical communication with said power supply means and said motor means for selectively operating said motor means from a non-operable condition in which the power supply means is electrically disconnected from the motor means to an operable condition in which the power supply means is electrically connected to the motor means and supplies power thereto; and transmission means located within the chamber of the housing and being driven by said motor means for dispensing of fluid from the carpule and through the needle at a controlled rate, said switch comprising a depressible lever pivotally mounted on said housing, said lever having a curved portion engagable with an axially slidable, annular sleeve which is disposed between the curved portion of the lever and the piston of the carpule, the arrangement is such that when the lever is pressed, the curved portion of the lever engages the annular sleeve for axially moving said annular sleeve towards the piston of the carpule thereby manually dispensing a small amount of fluid without engaging said power supply means and said motor means.

* * * * *